US008784872B2

(12) United States Patent
Oronsky et al.

(10) Patent No.: US 8,784,872 B2
(45) Date of Patent: Jul. 22, 2014

(54) FORMULATION FOR DECREASING TOBACCO, ALCOHOL, DRUG OR FOOD CONSUMPTION

(75) Inventors: Bryan T. Oronsky, Los Altos Hills, CA (US); Neil C. Oronsky, Los Altos Hills, CA (US); Arnold L. Oronsky, Los Altos Hills, CA (US)

(73) Assignee: Comgenrx, Inc., Mountain View, CA (US)

( * ) Notice: Subject to any disclaimer, the term of this patent is extended or adjusted under 35 U.S.C. 154(b) by 737 days.

(21) Appl. No.: 11/942,414

(22) Filed: Nov. 19, 2007

(65) Prior Publication Data

US 2009/0130178 A1   May 21, 2009

(51) Int. Cl.
*A61K 9/00* (2006.01)
*A61K 47/00* (2006.01)
*A61K 9/68* (2006.01)
*A61K 36/00* (2006.01)
*A61K 31/4168* (2006.01)
*A61K 9/12* (2006.01)
*A61K 9/70* (2006.01)

(52) U.S. Cl.
USPC ............. 424/440; 424/400; 424/43; 424/433; 424/618; 424/725; 514/401; 514/772

(58) Field of Classification Search
CPC ....... A24B 15/16; A61K 47/36; A61K 47/32; A61K 47/34; A61K 47/02; A61K 9/0056; A61K 9/08
USPC .................. 424/440, 400, 43, 433, 618, 725; 514/401, 772
See application file for complete search history.

(56) References Cited

U.S. PATENT DOCUMENTS

| | | | |
|---|---|---|---|
| 3,777,016 A | 12/1973 | Gilbert | |
| 4,361,585 A | 11/1982 | Edwards | |
| 4,764,378 A * | 8/1988 | Keith et al. | 424/435 |
| 5,008,106 A | 4/1991 | Merianos et al. | |
| 5,260,313 A | 11/1993 | Frome | |
| 5,294,438 A | 3/1994 | Chang et al. | |
| 5,336,486 A | 8/1994 | Acharya | |
| 5,401,728 A | 3/1995 | Simon | |
| 5,444,076 A | 8/1995 | Vasquez | |
| 5,472,685 A * | 12/1995 | Gaffar | 424/49 |
| 5,512,306 A * | 4/1996 | Carlsson et al. | 426/3 |
| 5,560,910 A | 10/1996 | Crandall | |
| 5,607,690 A | 3/1997 | Akazawa | |
| 5,654,337 A | 8/1997 | Roentsch et al. | |
| 5,824,359 A | 10/1998 | Khan et al. | |
| 5,885,597 A | 3/1999 | Botknecht et al. | |
| 5,908,846 A | 6/1999 | Bundgaard et al. | |
| 5,922,332 A | 7/1999 | Fossel | |
| 5,976,547 A | 11/1999 | Archer et al. | |
| 6,107,331 A * | 8/2000 | MacLean et al. | 514/428 |
| 6,132,762 A | 10/2000 | Cristobal | |
| 6,413,496 B1 | 7/2002 | Goodman et al. | |
| 6,479,074 B2 | 11/2002 | Murdock et al. | |
| 6,528,076 B2 | 3/2003 | Small | |
| 6,572,880 B2 | 6/2003 | Murdock et al. | |
| 6,638,981 B2 | 10/2003 | Williams et al. | |
| 6,730,667 B2 | 5/2004 | Deagle | |
| 6,923,982 B2 | 8/2005 | Barnes et al. | |
| 6,926,913 B2 | 8/2005 | Wormser et al. | |
| 2002/0042429 A1 * | 4/2002 | Myers et al. | 514/305 |
| 2002/0091074 A1 | 7/2002 | Wooley et al. | |
| 2003/0082214 A1 | 5/2003 | Williams et al. | |
| 2003/0125391 A1 * | 7/2003 | Jacobs et al. | 514/618 |
| 2003/0170296 A1 | 9/2003 | Sintov et al. | |
| 2004/0151771 A1 * | 8/2004 | Gin et al. | 424/468 |
| 2005/0004079 A1 | 1/2005 | Benjamin et al. | |
| 2005/0123619 A1 | 6/2005 | Farrell | |
| 2006/0280718 A1 | 12/2006 | Roy et al. | |
| 2007/0298100 A1 * | 12/2007 | Barras et al. | 424/464 |
| 2008/0102107 A1 | 5/2008 | Lewellyn et al. | |
| 2008/0311167 A1 | 12/2008 | Oronsky et al. | |
| 2008/0311217 A1 | 12/2008 | Oronsky et al. | |
| 2008/0311218 A1 | 12/2008 | Oronsky et al. | |
| 2008/0312583 A1 | 12/2008 | Oronsky et al. | |

(Continued)

FOREIGN PATENT DOCUMENTS

| | | |
|---|---|---|
| DE | 3622896 A1 | 1/1988 |
| EP | 0107376 A1 | 5/1984 |
| EP | 343807 A2 | 11/1989 |
| WO | WO-93/17695 A1 | 9/1993 |
| WO | WO-95/15169 A1 | 6/1995 |
| WO | WO-01/87234 A2 | 11/2001 |
| WO | WO-2004/010955 A2 | 2/2004 |
| WO | WO-2005/041988 A1 | 5/2005 |
| WO | WO-2010/009056 A2 | 1/2010 |

OTHER PUBLICATIONS

TheFreeDictionary, Terapetuic Definition, p. 1, 2009.*
Allen, Loyd V., Compounding Hard, Soft and Chewable Troches/Lozenges/Drops, International Journal of Pharmaceutical Compounding, vol. 3, No. 6, Nov./Dec. 1999, pp. 461-465.*
Polysorbate 20, Wikipedia, available Sep. 13, 2006, pp. 1-2.*

(Continued)

*Primary Examiner* — Robert T Crow
*Assistant Examiner* — Doan Phan
(74) *Attorney, Agent, or Firm* — Goodwin Procter LLP

(57) ABSTRACT

Formulations have been developed which assist individuals having an addiction such as smoking to reduce or quit engaging in the addictive behavior. Representative behaviors include smoking, excessive alcohol or food ingestion, drug addiction, and ingestion of caffeine or junk food providing quick "highs". The formulations assist the smoker to become dissatisfied with smoking, until he or she willingly gives up the habit or at least cuts down on the number of cigarettes smoked per day as an initial step towards quitting in the future. The formulations can also be used in conjunction with other known formulations, such as nicotine gum or patch. The formulations contain hydrophilic polymers, for example, polyethylene glycol (PEG) alone or in combination or polyvinyl pyrrolidone (PVP) (also known as povidone or polyvidone alone or in combination.), sweeteners and/or flavorings, viscosity modifiers/binders, and pH or buffering agents.

22 Claims, No Drawings

(56) References Cited

U.S. PATENT DOCUMENTS

| | | | |
|---|---|---|---|
| 2009/0048537 | A1 | 2/2009 | Lydon et al. |
| 2009/0117059 | A1 | 5/2009 | Oronsky et al. |
| 2009/0130048 | A1 | 5/2009 | Oronsky et al. |
| 2009/0130178 | A1 | 5/2009 | Oronsky et al. |
| 2009/0130182 | A1 | 5/2009 | Oronsky et al. |
| 2009/0131889 | A1 | 5/2009 | Oronsky et al. |
| 2010/0093673 | A1 | 4/2010 | Oronsky |
| 2010/0104614 | A1 | 4/2010 | Oronsky |

OTHER PUBLICATIONS

Santus, G. C. et al. Transdermal Enhancer patent literature (1993) J. Control. Rel. 25; pp. 1-20.
Stomach Pain.pdf (www.herbs2000.com/disorders/ stomach_pain.htm), 2003.
Hunger Pain website (http://www.wisegeek.com/what-are-hunger-pains.htm), 2011.
DiathermyWebsite.pdf (http://www.uihealthcare.com/topics/sportsmedicine/spor3327.html), 2001.
Dworkin, R.H. et al. Pharmacologic management of neuropathic pain: Evidence-based recommendations (2007) Pain. 132: 237-251.
Goodman & Gilman's, 10th Ed., col. 1, lines 48-53, pp. 587 and 607.
Loeser, J.D. et al. The Kyoto protocol of IASP Basic Pain Terminology (2008) Pain. 137; 473-477.
Mayhew, M.S. Controlling Neuropathic Pain (2008) J. Nurse Pract. 466-467.
International Search Report mailed on Apr. 19, 2010, for PCT Application No. PCT/US2009/050423, 6 pages.
Written Opinion mailed on Apr. 19, 2010, for PCT Application No. PCT/US2009/050423, 11 pages.
Galer, B. S. et al. "Topical diclofenac patch relieves minor sports injury pain: results of a multicenter controlled clinical trial," (2000) Journal of Pain and Symptom Management. 19(4):287-294.
IBSA Institut Biochemique SA: "Flector Patch (Diclofenac epolamine topical patch) 1.3%" [Online] Jun. 1, 2008, Daily Med Current Medication Information retrieved from the Internet: URL: http://dailymed.nlm.nih.gov/dailymed/drugInfo.cfm?id=7965.
"Look after your feet and your feet will look after you (Compeed Blister Plasters)" [Online] Sep. 18, 2006, Retrieved from the Internet: URL: http://www.dooyoo.co.uk/first-aid/compeed-blister-plasters/1036886/.
International Search Report mailed on Jun. 16, 2009, for PCT Application No. PCT/US2008/084064, 4 pages.
Written Opinion mailed on Jun. 16, 2009, for PCT Application No. PCT/US2008/084064, 11 pages.
"Polyethylene Glycol 3350" Miralax Product Information, Retrieved from the Internet: URL: http://www.miralax.com/miralax/hcp/productinformation.jsp, Apr. 24, 2009.
Bundesverband Der Pharmazeutischen Industrie: "Rote Liste Arzneimittelverzeichnis für Deutschland" 2004, ECV Editio Cantor Verlag Aulendorf, Frankfurt/Main, p. 63048, paragraphs 63045, 63040-p. 63059; XP-002525783.
Bundesverband Der Pharmazeutischen Industrie: "Rote Liste Arzneimittel für Deutschland" 2004, ECV Editio Cantor Verlag Aulendorf, Frankfurt/Main, p. 56058, paragraph 56061; XP-002525784.
Bundesverband Der Pharmazeutischen Industrie: "Rote Liste" 2004, ECV Editio Cantor Verlag Aulendorf, Frankfurt/Main, p. 109, lines 23-40, p. 67225, paragraph 67213 and p. 67238, paragraph 67237; XP-002525785.
"British National Formulary" (2000) British Medical Association, pp. 54-55; XP-002525871.
Adams-Graves, P. et al. (1997). "RheothRx (Poloxamer 188) Injection for the Acute Painful Episode of Sickle Cell Disease: A Pilot Study," Blood 90(5): 2041-2046.
Dodd, V. et al. (Jul. 2003). "Comparing the Use of Hydrogel Dressings to Lanolin Ointment With Lactating Mothers," J. Obstet. Gynecol. Neonatal Nurs. 32(4):486-494.
International Search Report mailed on Sep. 25, 2008, for PCT Application No. PCT/US2008/007354, 3 pages.
International Search Report mailed on Apr. 9, 2009, for PCT Application No. PCT/US2008/084062, 5 pages.
Levy, D. et al. (May 1998). "Local Nitric Oxide Synthase Activity in a Model of Neuropathic Pain," Eur. J. Neurosci. 10(5):1846-1855.
Millan, M.J. (Jan. 1999). "The Induction of Pain: An Integrative Review," Progress in Neurobiology 57(1):1-164.
Murdan, S. (Jul.-Aug. 2005). "A Review of Pluronic Lecithin Organogel as a Topical and Transdermal Drug Delivery System," Hospital Pharmacist 12(7):267-270.
Rowley, T.J. et al. (Apr. 2005). "The Role of Adrenergic and Cholinergic Transmission in Volatile Anesthetic-Induced Pain Enhancement," Anesth Analg. 100(4):991-995.
Walsh, K.E., "Safety and Efficacy of Topical Nitroglycerin for Treatment of Vulvar Pain in Women with Vulvodynia: A Pilot Study," <http://www.ourgyn.com/contentlindex2.php?option=com_content&do_pdf=1&id=16>, accessed Oct. 24, 2007.
Written Opinion mailed on Sep. 25, 2008, for PCT Application No. PCT/US2008/007354, 6 pages.
Written Opinion of the International Searching Authority mailed on Apr. 9, 2009, for PCT Application No. PCT/US2008/084062, 6 pages.
International Preliminary Report on Patentability and Written Opinion mailed on Jan. 13, 2011, for PCT Application No. PCT/US2009/048942, 8 pages.
http://lifewave.wordpress.com; available at least by Dec. 13, 2007; accessed online May 2011.
Assandri, A., et al. Local tolerability and pharmacokinetic profile of a new transdermal delivery system, diclofenac hydroxyethylpyrrolidine plaster, Drugs Exp. Clin. Res. (1993); 19(3); p. 89-95.
STN search results for diclofenac epolmamine, Mar. 17, 1989.
TheFreeDictionary, Therapeutic Definition, p. 1, 2009.
Allen, Loyd., Compounding Hard, Soft and Chewable Troches/Lazenges/Drops, International Journal of Pharmaceutical Compounding, vol. 3 No. 6, Nov./Dec. 1999, pp. 461-465.
"Vehicle" as defined by Stedman's Medical Dictionary 28th Ed. (2005); Lippincott Williams & Wilkins.
Willimann, H. L., et al. Lecithin organogels as matrix for the transdermal transport of drugs, Biochem, Biophys. Res. Commun. (1991); 177(3); pp. 897-900.
Ichinose, M. et al. Protection against bradykinin-induced bronchoconstriction in asthmatic patients by neurokinin receptor antagonist, The Lancet (1992) 340(8830); 1248-1251.
Maddox, L. et al. The Pathophysiology of Asthma, Annu. Rev. Med 92002) 53; 477-498.
Sonopuncture Ulrasound website; http://www.drmanik.com/chap8.htm; accessed Apr. 12, 2011; available at least by Jan. 16, 2006.
International Search Report mailed on Aug. 3, 2010, for PCT Application No. PCT/US2009/048942, 4 pages.
Siegert, Wolfgang, "Microbiological Quality Management for the Production of Cosmetics and Toiletries," Cosmetic Science Technology 2005, pp. 189-195.

\* cited by examiner

FORMULATION FOR DECREASING TOBACCO, ALCOHOL, DRUG OR FOOD CONSUMPTION

FIELD OF THE INVENTION

Formulations which decrease urges associated with addictions such as smoking, drug or alcohol abuse, and overeating (leading to obesity), and methods of use thereof have been developed.

BACKGROUND OF THE INVENTION

Smoking represents an enormous public health problem, and yet in spite of widespread agreement about the deleterious health effects of tobacco to the smoker from atherosclerotic vascular disease, cancer, and chronic obstructive pulmonary disease, to the non-smoker from second-hand smoke, and to society which bears most of the expense of smoking-related illness, the practice continues and actually is increasing among adolescents and minorities and in certain parts of the world. The view of cigarette smoking as compulsive behavior in the face of negative consequences can also be applied to other compulsions related to caffeine consumption, eating of sugar or fat-laden foods, abuse of alcohol, barbiturates, recreational and illicit drugs and narcotics.

Smoking is as much a habit as it is a behavior which is why a multimodal approach, rather than a single strategy, is often necessary to treat this complex behavior. A multimodal approach also often forms the basis of the treatment of other compulsive behaviors such as overeating, drinking alcohol and taking drugs. In short, since all individuals with detrimental or compulsive habits do not share the same triggers, the relative efficacy of any one treatment depends on the person trying to quit. It follows therefore that the more options available to these individuals the greater the likelihood of success. For example, the conventional wisdom is that tobacco abuse is primarily fueled by nicotine dependence, and while this may be at the core of the addiction, other smoking-related stimuli, in particular, the taste and flavor of a cigarette, can accentuate the nicotine buzz and trigger the craving for a smoke.

The most consistent clinical benefit for smoking comes from pharmacologic strategies including nicotine replacement in the form of patches, gum and lozenges, antidepressants such as Buproprion, and, most recently, a nicotine receptor stimulant called Varenicline which, according to a Cochrane review article, nearly triples the odds of stopping smoking. However, these pharmacologic anti-smoking remedies can be expensive, generally have unwanted side effects and, moreover, given the complex nature of smoking, their efficacy is not always guaranteed. The same can often be said of anti-alcohol, anti-drug, and anti-obesity remedies.

It is therefore an object of the present invention to provide formulations for use in reducing addictions while avoiding the side effects of the known prescription anti-smoking, anti-alcohol, anti-drug, and anti-obesity remedies.

It is a further object of the invention to provide formulations over-the-counter formulations, which do not contain any "active" ingredients requiring regulatory approval as a new drug.

It is still another object of the present invention to provide formulations which can be used repeatedly and reacts with cigarettes, food, caffeine, drugs, alcohol and other tobacco products to leave behind an unpleasant taste or sensation while providing oral and manual stimulation to replace the rituals of tobacco, drugs, caffeine, alcohol, or food.

SUMMARY OF THE INVENTION

Formulations have been developed which assist individuals having an addiction such as smoking to reduce or quit engaging in the addictive behavior. Representative behaviors include smoking, excessive alcohol or food ingestion, drug addiction, and ingestion of caffeine or junk food providing quick "highs". The formulations assist the smoker to become dissatisfied with smoking, until he or she willingly gives up the habit or at least cuts down on the number of cigarettes smoked per day as an initial step towards quitting in the future. The formulations can also be used in conjunction with other known formulations, such as nicotine gum or patch. The formulations contain hydrophilic polymers, for example, polyethylene glycol (PEG) alone or in combination or polyvinyl pyrrolidone (PVP) (also known as povidone or polyvidone alone or in combination.), sweeteners and/or flavorings, viscosity modifiers/binders, and pH or buffering agents.

In another preferred embodiment, the formulation is a rapidly dissolving sublingual composition comprising:
 (a) a rapidly dissolving base comprising a polyethylene glycol such as PEG 3350, mannitol, sodium bicarbonate, citric acid, and sucrose,
 (b) acesulfame potassium
 (c) Stevia and
 (d) a flavoring such as raspberry flavor concentrate
In another embodiment, the formulation comprises
 (a) PEG MW 1450 60 g,
 (b) PEG MW 4500 11 g,
 (c) a dessicant such as silica gel 0.56 g,
 (d) a viscosity modifying agent such as acacia 0.56 g,
 (e) polysorbate 80 3.75 ml, and
 (f) an artificial sweetener such as nutrasweet 0.56 g and (g) sodium saccharine 0.28 g.

In another embodiment, the formulations can be made into a cigarette or cigar shape which can be placed under the tongue and allowed to dissolve slowly, reducing the pharmacologic desire to smoke. The cigar or cigarette shaped preparation may be removed from the mouth at any time and played with, simulating the holding and ashing rituals of smoking.

The clinical results described in the examples demonstrate that the formulations suppress the desire or need to smoke, especially among more casual users, primarily by interfering with the taste, flavor and enjoyment of the cigarette so that the act of smoking loses its appeal. In some cases, if the patient smoked after intake of the preparation or inhaled the smoke of other people's cigarettes, he or she felt physically unwell, for example, nauseous. The examples further demonstrate that, at least in one subject, the formulation was also effective in spoiling the pleasure of drinking coffee. In two subjects, the preparation interfered with the taste of alcohol. In others, it ruined the taste of food and dessert and made chewing tobacco unappealing.

Given the magnitude of the smoking problem and the enormous burden it represents in terms of death and disability, it is highly desirable to provide a method and composition which facilitates lowering the incidence of tobacco smoking by affecting the taste and flavor of a cigarette in the mouth of an individual. These preparations, lacking any "active" ingredients, can be used repeatedly to replace cigarettes completely in the case of those who quit, as well as by smokers to reduce consumption. The formulations have the advantage of being inexpensive to manufacture, providing oral stimulation to the user, and not containing any prescription or regulated substances.

DETAILED DESCRIPTION OF THE INVENTION

I. Formulations

A. Hydrophilic Polymers

"Water Soluble" as used herein refers to substances that have a solubility of greater than or equal to 5 g/100 ml water.

"Hydrophilic" as used herein refers to substances that have strongly polar groups that readily interact with water.

1. Polyalkylene Oxides

Topical compositions having as the active ingredient a polyalkylene oxide homopolymer, copolymer, or combinations thereof have been developed and tested. The formulation typically includes excipients that are used to form a cream, gel, lotion, spray, foam, paste, patch, suspension or dispersion, for topical application to the skin or mucosal surface.

The active ingredient can be a hydrophilic polymer, such as polyethylene glycol ("PEG", also referred to a polyethylene oxide ("PEO")) or polyethylene oxide-co-propylene oxide ("PEO-PPO") copolymers (available under the trade name Pluronics®), alone or in combination with mono or diesters of a hydrophilic polymer (e.g., polyoxyl 40 stearate).

PEG is prepared by the polymerization of ethylene oxide. PEG is typically a liquid or low-melting solid at room temperature depending on the molecular weight of the polymer. Poly (ethylene glycol) is produced by interaction of calculated amount of ethylene oxide with water, ethylene glycol or ethylene glycol oligomers. The reaction can be catalyzed by acidic or basic catalysts. Depending on the catalyst type the mechanism of polymerization can be cationic or anionic. Anionic mechanism is more preferable because it allows one to obtain PEG with low polydispersity. Polymerization of ethylene oxide is an exothermic process. Polyethylene oxide or high-molecular polyethylene glycol can be synthesized by suspension polymerization.

2. Povidone

Povidone, or polyvinylpyrrolidone, is a hydrophilic polymer that is available from a variety of sources and frequently used as one of many pharmaceutical excipients, typically as a lubricating agent.

3. Pluronics

Pluronics®, also known as poloxamers, are block copolymers containing ethylene oxide and propylene oxide. Pluronics® have been used as antifoaming agents, wetting agents, dispersants, thickeners, and emulsifiers. Because of their amphiphilic structure, poloxamers have surfactant properties that make them useful in industrial applications. Among other things, they can be used to increase the water solubility of hydrophobic, oily substances or otherwise increase the miscibility of two substances with different hydrophobicities. For this reason, these polymers are commonly used in industrial applications, cosmetics, and pharmaceuticals. They have also been used as model systems for drug delivery applications.

Pluronic® F-127 is a polaxamer surfactant which is an ABA-type block copolymer containing 70% polyethylene oxide (PEO). The molecular weight is 12,500 Daltons. Upon cooling, Pluronic® F-127 becomes a liquid, while at higher temperatures, the material is a solid or semi-solid. DMSO and lecithin/isopropyl palmitate can be added to Pluronic® F-127 to increase absorption through the skin.

B. Excipients

The hydrophilic polymer can be applied as a solution, for example, dissolved in water or an aqueous solution and administered with a cotton tipped swab, as a film, sprayed, to dabbed onto a surface.

The hydrophilic polymer may also be formulated with one or more excipients to form a tablet, troche, gum, gel, mouth strip, emulsion, or foam.

A "troche" is a small medicated wafer or lozenge which is designed to dissolve, typically under the tongue.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", 4$^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxypropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "paste" is a liquid or emulsion having solid material homogenously suspended therein, typically in a lotion cream or gel.

A "gel" is a composition containing a thickening agent or polymeric material dissolved or suspended in a liquid. The liquid may include a lipophilic component, an aqueous component or both. Some emulsions may be gels or otherwise include a gel component. Some gels, however, are not emulsions because some do not contain a homogenized blend of immiscible components.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetypyridinium chloride, chlorobutanol, phenol, phenylethyl alcohol, and thimerosal.

III. Methods of Administration

In one embodiment, the formulation is applied as a solution, either by dabbing, swabbing, swishing (mouth wash) or spraying onto the mucosal surfaces of the mouth. In a preferred embodiment, the formulation is provided in a personal spray bottle that can be kept in a purse or shirt pocket for ready use.

In another embodiment, the formulation is in the form of a solid tablet, lozenge, mint, or troche, which is placed under the tongue where it slowly dissolves. These are typically provided in a blister pack, preferably in multiples of two for ready use. The formulation may also be provided as chewing gum The amount of formulation used will depend on the individual. As demonstrated by the examples, some people require much more material than others to have an effect. Since there is no regulated therapeutic agent, a person may continue to administer the formulation until the desired effect is achieved.

The formulation can also be provided as part of a kit containing hydrophilic polymer, such as PEG or polyvinylpyrrolidone alone or in combination, with one or more of the following items:

nicotine gum, nicotine inhaler, nicotine lozenges, nicotine nasal spray, transdermal nicotine patches, nicotine tablets and capsules, antidepressants, mood stabilizers, self help materials, hypnosis tapes and literature, anti-smoking, anti-obesity, anti-drug and anti-addiction literature and pictures, questionnaires, herbal preparations such as Kava Kava and Chamomile, artificial cigarettes, cigars and pipes, anti-smoking cigarette filters, different prescription, over-the-counter and herbal anti-obesity therapies, antabuse, flagyl (has antabuse-like effects), naloxone (Narcan), silver acetate, clonidine, benzodiazepines, and antipsychotics.

The present invention will be further understood by reference to the following non-limiting examples.

PEG 300 mw Liquid

PEG 300 is used neat and applied as a liquid using a cotton tipped swab.

Povidone Liquid

½ teaspoon of Povidone USP (30) powder was mixed with about 2 mls of bottled water. This is applied using a cotton tipped swab.

PEG 3350 Sublingual Composition (a) rapidly dissolving base comprising a polyethylene glycol such as PEG 3350, mannitol, sodium bicarbonate, citric acid, and sucrose (b) acesulfame potassium (c) Stevia and (d) a flavoring such as raspberry flavor concentrate PEG 1450/4500 Sublingual Composition (a) PEG MW 1450 60 g (b) PEG MW 4500 11 g (c) silica gel 0.56 g (d) acacia 0.56 g (e) polysorbate 80 3.75 ml (f) an artificial sweetener such as nutrasweet 0.56 g and (g) sodium saccharine 0.28 g Example 1

Administration of PEG 300 Liquid to Decrease Smoking

The subject is in her 50's and is a 20 pack year smoker. PEG MW 300 was applied to a sterile Q-tip which the subject rubbed on her gums and placed under her tongue. She then tried to smoke a cigarette but claimed that cigarette "tasted awful" and she stubbed it out.

Example 2

Administration of PEG 3350 Composition to Decrease Smoking

A. A Caucasian female in her late forties who smokes a pack and a half of cigarettes a day was given 4 sublingual trochees. When she had the urge to smoke, she put one or more tablets under her tongue at a time, waited until they dissolved, and then smoked a cigarette. She reported that with 1-2 tablets she had very little or no effect but with 3 or 4 sublingual pills at a time the cigarette lost its taste and, as a result, she would only take a couple of puffs before stubbing it out. The effect lasted for about an hour before the taste of the cigarette returned. Whenever the subject desired a cigarette, she popped 3 or 4 lozenges into her mouth and, although she continued to smoke, she did not finish any of the cigarettes.

B. A thirty year old Caucasian woman who smokes one pack of cigarettes a day was given 5 sublingual trochees and reported that if she smoked after placing 3-4 tablets under her tongue she became physically ill and threw up.

C. A male in his sixties, self-described as a "casual" and intermittent smoker, reported that the use of 1-2 sublingual trochees interfered with the taste of the cigarette such that he did not finish the cigarettes and felt that if he was given a supply of these trochees he would lose the urge to smoke D. A self-described "chain smoker" in his thirties reported that the administration of sublingual lozenges or trochees in any amount "possibly" interfered with the taste of the cigarette but had no effect on curbing his desire to smoke E. A woman in her seventies reported that the sublingual trochees in any amount had absolutely no effect on her desire to smoke F. A man in his forties reported that the administration of 3-4 sublingual trochees before he smoked completely took away the taste of the cigarette so that he "didn't see the point to smoking the cigarette anymore" and put it out.

G. A woman in her early thirties and an intermittent smoker reported that the administration of 3-4 sublingual trochees before she smoked completely took away the taste of the cigarette.

H. The subject is in her 40's and is an inveterate smoker. After administration of 3 sublingual trochees, the patient went to smoke but stated that the experience was similar to smoking her first cigarette: she felt nauseated, lightheaded and the cigarette had such a "nasty" taste that she put it out I. The smoker is in his 40s and has been smoking 1-2 packs a day since the age of 12. He stated that although the trochees had no effect on the taste of the cigarette or his desire to smoke he noticed that over the next few days he had less of a craving to smoke Example 3

Administration of PEG 1450/4500 Formulation to Decrease Tobacco Consumption

The subject is in his 20s and regularly uses chewing tobacco throughout the day. He put 1 trochee of PEG 1450/4500, a waxy, slowly dissolving substance, in between his cheek and gum and at the same time packed a pinch or "dip" of chewing tobacco. He stated that the trochee so completely took away the taste of the chewing tobacco that he took the tobacco out of his mouth. Moreover, because the trochee was slowly dissolving, it substituted well for the pinch of chewing tobacco.

Example 4

Administration of Formulation to Decrease Caffeine Consumption

A. A man in his 50's drinks about 2 pots of coffee a day. After putting 1 trochee PEG 3350 under his tongue he tried to drink a cup of coffee but the taste was "ruined" both immediately following sublingual administration and several hours after Example 5

Administration of Formulation to Decrease Alcohol Consumption

A. The subject is in her 40s and drinks 1-2 beers a day. After sublingual administration of 2 trochees PEG 3350, the subject tried to drink a beer but became nauseated and had to put it down Example 6

Administration of Povidone to decrease smoking

A. The subject is in her 50's and smokes about a pack a day. Povidone USP was applied with a sterile cotton tipped applicator was dipped into the mixture and rubbed on her gums and under her tongue. She commented that when immediately after when she went to smoke a cigarette it tasted "awful" and she put it out.

B. The subject is in her 40s and smokes about a pack and a half a day of mentholated cigarettes. Povidone was applied to a sterile cotton tipped applicator was dipped into the mixture and rubbed on her gums and under her tongue. She commented that the Povidone/water mixture made her mouth feel numb and when immediately after when she went to smoke a cigarette it tasted "like a regular cigarette" not mentholated but this did not cause her to want to put the cigarette out.

C. The subject is in his 30s and smokes about a pack a day of cigarettes. The subject poured the Povidone mixture in his mouth, swished it around and spit it out. Commenting that his tongue and mouth felt numb, he tried to smoke a cigarette but it had a "bad taste" and he put it out. He stated that if this mixture were used regularly prior to wanting a smoke it would probably induce him to quit.

D. The subject is in her early 40s and has advanced chronic obstructive pulmonary disease ("COPD") due to a 20 year history of smoking about two packs a day of unfiltered clove cigarettes. A sterile cotton-tipped applicator was dipped into Povidone and rubbed on her gums and under her tongue. She went to smoke and even though the taste of the cigarette was "ruined" for her she smoked it all anyway. She stated however that if she were to use this mixture regularly she might be induced to smoke less.

E. The subject of example 3 dipped a sterile cotton tipped applicator into Povidone and rubbed it on her gums and under his tongue prior to placing a pinch of chewing tobacco in his mouth. The mixture did not make his mouth numb, had "absolutely no effect" on the taste of the chewing tobacco and therefore did not curb his desire to use it.

Example 7

Administration of Povidone to Decrease Appetite or Alcohol Consumption

A. The subject is in her 30s, describes herself as "slightly overweight" and wants to look skinnier. Povidone was applied with a sterile cotton tipped applicator was dipped into the mixture and rubbed on her gums and under her tongue a few minutes before lunchtime. Although she was very hungry and was looking forward to eating, she claimed that the food tasted "nasty" and took away her desire to eat.

B. The subject is in her 40s with a self-described sweet-tooth and a BMI of 28. She dipped a sterile cotton tipped applicator into Povidone and rubbed it on her gums and under her tongue. A few minutes later she put a spoonful of rocky road ice cream in her mouth but because it had no taste she did not continue eating it. A few hours later she went to have another spoonful of ice cream but it still had no taste for her so she did not continue eating it.

C. This is an obese subject in his 50s who, after swishing Povidone liquid in his mouth, went to eat a meal, but did not finish it because it had no taste.

D. The subject is in her 40s and went to drink a margarita after swishing and spitting a Povidone. The alcoholic drink "tasted funny" and so she did not wish to finish it.

We claim:

1. A method of decreasing a subject's desire for tobacco, alcohol, or drugs, comprising administering orally to the subject a formulation comprising an effective amount of a hydrophilic polymer composition, as the only active ingredient, selected from the group consisting of a polyalkylene oxide, polyvinylpyrrolidone, poloxamer, combination of polyethylene glycol and polyvinylpyrrolidone, and combination of two polyethylene glycols having different molecular weights; wherein the formulation is administered to the subject prior to smoking or chewing tobacco, drinking alcohol or taking drugs, to thereby decrease the subject's desire for tobacco, alcohol, or drugs.

2. The method of claim 1 wherein the hydrophilic polymer composition is selected from the group consisting of polyethylene glycol, polyvinylpyrrolidone, and combinations thereof.

3. The method of claim 1 wherein the formulation comprises polyethylene glycol 3350 as the only active ingredient, mannitol, sodium bicarbonate, citric acid, and sucrose.

4. The method of claim 1 wherein the only active ingredient in the formulation is a mixture of polyethylene glycol 1450 and polyethylene glycol 4500.

5. The method of claim 4 wherein the formulation further comprises a sweetener or flavoring.

6. The method of claim 5 wherein the formulation comprises a mixture of polyethylene glycol 1450 and polyethylene glycol 4500 as the only active ingredient, silica gel, acacia, polysorbate 80, and sweetener.

7. The method of claim 1 wherein the formulation further comprises one or more of colorants, sweeteners, flavorants, excipients, binders, coating agents, and lubricants.

8. The method of claim 1 wherein the formulation further comprises a mucoadhesive which adheres the formulation to nasal or oral mucosa for an effective period of time.

9. The method of claim 1 wherein the method is to decreasing a subject's desire for tobacco; and the formulation is administered to the subject prior to smoking or chewing tobacco, to thereby decrease the subject's desire for tobacco.

10. The method of claim 9 wherein the hydrophilic polymer composition is polyethylene glycol, polyvinylpyrrolidone, or a combination thereof.

11. The method of claim 9 wherein the hydrophilic polymer composition is polyethylene glycol.

12. The method of claim 9 wherein the hydrophilic polymer composition is polyethylene glycol 3350.

13. The method of claim 9 wherein the hydrophilic polymer composition is a combination of two polyethylene glycols having different molecular weights.

14. The method of claim 9 wherein the hydrophilic polymer composition is a mixture of polyethylene glycol 1450 and polyethylene glycol 4500.

15. The method of claim 9 wherein the hydrophilic polymer composition is polyvinylpyrrolidone.

16. The method of claim 11 wherein the formulation is in the form of a sublingual troche.

17. The method of claim 13 wherein the formulation is in the form of a sublingual troche.

18. The method of claim 1 wherein the method is to decreasing a subject's desire for alcohol; and the formulation is administered to the subject prior to drinking alcohol, to thereby decrease the subject's desire for alcohol.

19. The method of claim 18 wherein the hydrophilic polymer composition is polyethylene glycol, polyvinylpyrrolidone, or a combination thereof.

20. A method of decreasing a subject's desire for food, comprising administering orally to the subject a formulation comprising an effective amount of a hydrophilic polymer composition, as the only active ingredient, selected from the group consisting of a polyalkylene oxide, polyvinylpyrrolidone, poloxamer, combination of polyethylene glycol and polyvinylpyrrolidone, and combination of two polyethylene glycols having different molecular weights; wherein the formulation is administered to the subject prior to eating or drinking, to thereby decrease the subject's desire for food.

21. The method of claim 20 wherein the hydrophilic polymer composition is polyethylene glycol, polyvinylpyrrolidone, or a combination thereof.

22. The method of claim 20 wherein the hydrophilic polymer composition is polyvinylpyrrolidone.

* * * * *